United States Patent [19]

Shipchandler

[11] 4,051,128
[45] Sept. 27, 1977

[54] STEROID ETHERS

[75] Inventor: Mohammed T. Shipchandler, TerreHaute, Ind.

[73] Assignee: IMC Chemical Group, Inc., Terre Haute, Ind.

[21] Appl. No.: 709,693

[22] Filed: July 29, 1976

[51] Int. Cl.² ............................................. C07J 71/00
[52] U.S. Cl. ................................................ 260/239.57
[58] Field of Search ............... 260/397.5, 397.4, 293.57

[56] References Cited

U.S. PATENT DOCUMENTS 3,828,081  8/1974  Ercoli et al. ..................... 260/397.2
3,989,828  11/1976  Aries ............................... 260/397.4

Primary Examiner—Elbert L. Roberts
Attorney, Agent, or Firm—Edward A. Figg; Howard E. Post

[57] ABSTRACT

Novel steroid ethers are disclosed, which are represented by the formula:

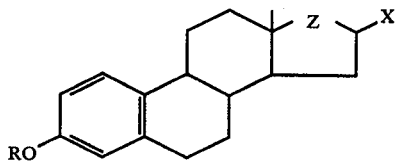

wherein Z is selected from the group consisting of >C=O >CHOH, and

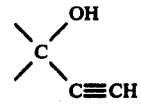

X is selected from the group consisting of —H and —OH, and R is selected from the group consisting of

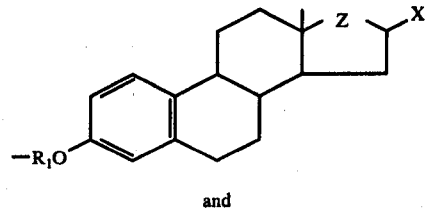

and

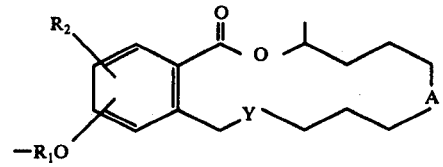

wherein $R_1$ is a straight or branched chain hydrocarbon of from 1 to about 16 carbon atoms; A is selected from the group consisting of —$CH_2$—, >C=O, and >$CHOR_3$; Y may be a single bond or a double bond; $R_2$ and —$R_1O$— represent substituents on the aromatic ring of the group of the second formula, in either the 2 or 4 positions, and $R_2$ is selected from the group consisting of H and $OR_3$; $R_3$ is selected from the group consisting of lower alkyl of from 1 to about 6 carbon atoms; lower acyl of from 1 to about 6 carbon atoms; monocyclic aryl of about 6 to 8 carbon atoms; and monocyclic aralkyl, that is, an alkyl group having an aryl substituent thereon, wherein the alkyl group has 1 to about 5 carbon atoms and the aryl group has about 6 to 8 carbon atoms. Also disclosed are methods for making the above compounds.

11 Claims, No Drawings

STEROID ETHERS

The present invention relates to novel compounds sometimes referred to herein as steroid ethers and to methods for their production and use. More particularly, the invention relates to compounds represented by the formula:

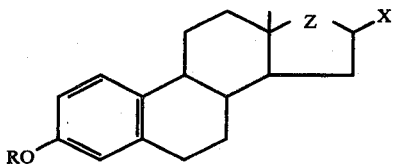

wherein Z is selected from the group consisting of >C=O >CHOH, and

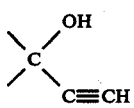

X is selected from the group consisting of —H and —OH and R is selected from the group consisting of

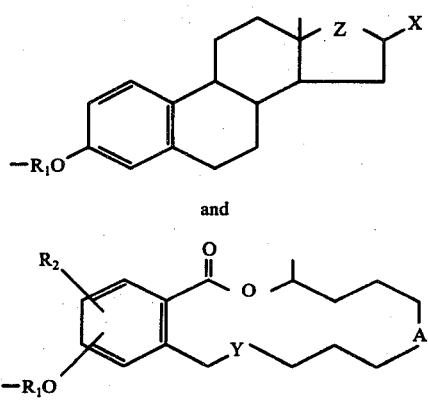

wherein $R_1$ is a straight or branched chain hydrocarbon of from 1 to about 16 carbon atoms, such as propyl, butyl, octyl, 3-ethylhexyl, etc.; A is selected from the group consisting of —CH$_2$—, >C=O, and >CHOR$_3$; Y may be a single bond or a double bond; $R_2$ and —R$_1$O— represent substituents on the aromatic ring of groups of the second formula, in either the 2 or 4 positions and $R_2$ is selected from the group consisting of H and OR$_3$; $R_3$ is selected from the group consisting of lower alkyl of from 1 to about 6 carbon atoms, such as methyl, ethyl, propyl, butyl, pentyl, and hexyl; lower acyl of from 1 to about 6 carbon atoms, such as formyl, acetyl, butyroyl, etc.; monocyclic aryl of about 6 to 8 carbon atoms, such as phenyl, tolyl, etc.; and monocyclic aralkyl, that is an alkyl group having an aryl substituent thereon, wherein the alkyl group has 1 to about 5 carbon atoms and the aryl group has about 6 to 8 carbon atoms, such as benzyl, toylmethyl, etc.

Alternatively stated, the present invention encompasses compounds comprising two steroid moieties of the estrone type bonded together through a hydrocarbon chain and ether linkages and compounds comprising a steroid moiety of the estrone type and a zearalin bonded together through a hydrocarbon chain and ether linkages.

As used herein, the term "zearalin" refers to the class of compounds having the basic chemical skeletal formula set forth below, and includes such compounds as zearalenone, zearalanol, zearalenol, etc.

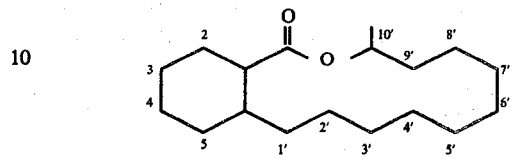

Unless otherwise indicated, the compounds of this invention are not intended to be limited to any particular isomeric configuration, and, more specifically, when Y is a double bond, the configuration at that bond may be either cis or trans. The nomenclature used herein, insofar as it relates to zearalins, generally conforms to that described by Shipchandler, M. T., *Heterocycles* 3, 471 (1975).

The steroid ethers of this invention exhibit a variety of hormonal activities in animals. Certain of the compounds possess estrogenic activity or aid in increasing the rate of growth in meat-producing animals, e.g. cattle, lamb, swine, etc. Others of the compounds exhibit anti-androgenic activity in animals.

The compounds of this invention can be administered to animals by any suitable method, including oral and parenteral administrations. For example, the compounds can be blended with ordinary feed containing nutritional values in an amount sufficient to produce the desired pharmacological response, and, thus, be fed directly to the animals. Parenteral administration of the compounds may be by injection of a suitable suspension medium, such as peanut oil, containing the desired compound, or by subcutaneous implantation of a suitable implant pellet containing such compound.

When a steroid ether is to be administered in feeds, an animal feed composition may be prepared containing the usual nutritionally-balanced quantities of carbohydrates, proteins, vitamins and minerals, together with an effective amount of a steroid ether. Some of these usual dietary elements are grains, such as ground grain and grain byproducts; animal protein substances, such as those found in fish meal and meat scraps; vegetable proteins, such as soybean oil meal or peanut oil means; vitaminaceous materials, e.g. vitamin A and D mixtures, riboflavin supplements, and other vitamin B complex members; and bone meal and limestone to provide minerals. A conventional type of feed material for use with cattle includes alfalfa hay and ground corn cobs together with supplementary vitaminaceous substances if desired.

The steroid ethers may consist of two similar steroid moieties bonded together through a hydrocarbon chain, or may consist of dissimilar steroid moieties, or a steroid moiety and a zearalin. The steroids used as starting materials are well-known compounds, e.g. estrone, estradiol, estratriol, etc., and are generally available commercially. The preferred steroid starting material is estrone.

In compounds containing a zearalin group, the zearalin used as a starting material may be prepared from zearalenone, which has the following structure.

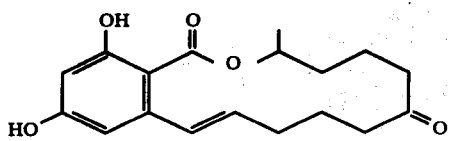

Zearalenone is a natural fermentation product resulting from the cultivation of a zearalenone-producing strain of the microorganism *Giberella zeae* on a suitable nutrient medium. The production of zearalenone is described in U.S. Pat. No. 3,196,019 issued to Andrews, F. N. et al. on July 20, 1965.

The steroid ethers are prepared by reacting a steroid, a mixture of steroids, or a mixture of a steroid and a zearalin with a dihaloalkane under etherifying conditions. The particular compounds used as starting materials depend on the desired end product. The steroid starting materials are represented by the following formula:

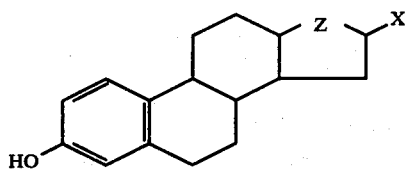

wherein Z and X are defined as in the steroid ethers above.

To prepare compounds containing a zearalin group, a zearaline starting material represented by the following formula is employed:

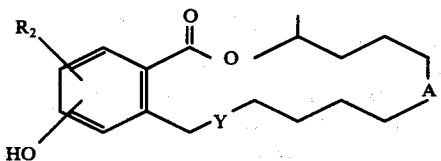

wherein the substituents A, $R_2$, and Y are defined as in the steroid ethers above. The preferred zearalin starting materials are zearalenone, zearalanone (wherein A is >C=O, Y is a single bond, and the aromatic ring is substituted in the 2 and 4 positions with hydroxyl groups), zearalane (wherein A is —$CH_2$—, Y is a single bond, and the aromatic ring is substituted in the 2 and 4 positions with hydroxyl groups), and zearalanol (wherein A is >CHOH, Y is a single bond, and the aromatic ring is substituted in the 2 and 4 positions with hydroxyl groups).

If a steroid ether having identical steroid groups is desired, then a substantially pure steroid is used as the starting material. If a steroid ether having dissimilar steroid groups is desired then a mixture of the two desired steroids may be used as the starting material. If a steroid ether having a steroid group and a zearalin group is desired, then a mixture of the appropriate steroid and zearalin may be used as the starting material.

When two dissimilar starting materials are employed, the resulting product may include three ether compounds: one of which will have identical groups of one structure, the other will have identical groups of the second structure, and the third will have the two different groups. The three ether compounds may be separated, for instance, by conventional chromatography techniques, if desired.

Alternatively, one starting material, e.g. a steroid or a zearalin may be pre-reacted with a dihaloalkane under etherifying conditions to provide a haloalkyl derivative, which may then be reacted with the other starting material to produce the desired product. This procedure is exemplified by the following reaction scheme:

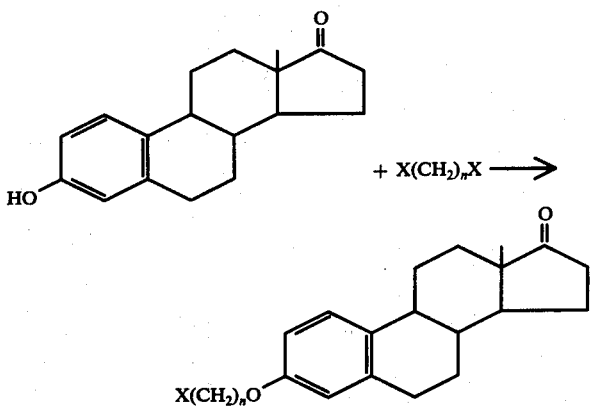

X is halo, *n* is an integer 1-6

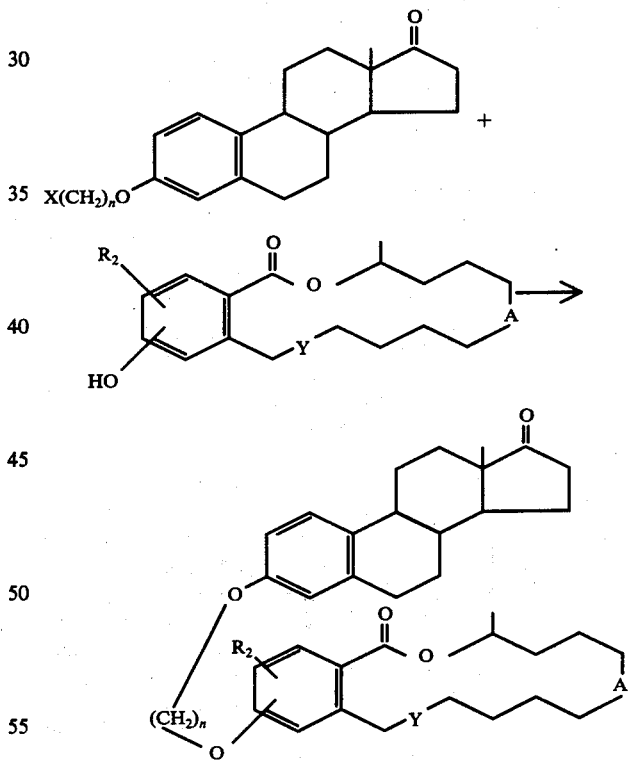

The selection of the dihaloalkane for the reaction will depend, in part, upon the length of the hydrocarbon chain through which the groups of the steroid ethers are bonded. Generally a hydrocarbon chain of from 1 to about 16 carbon atoms is desired, thus indicating the use of a dihaloalkane having that number of carbon atoms. The preferred dihaloalkane has about 2 to 10 carbon atoms, most preferably about 3 to 6 carbon atoms. The dihaloalkane may have a straight or branched hydrocarbon chain, and the halo substituents thereon may be fluoro, chloro, bromo or iodo, but are preferably bromo or chloro groups. Exemplary of preferred dihaloalkanes are 1,4-dibromobutane, 1,3-dichloropropane, 1,5-dibromopentane, 1,6-dibromohexane, 3-ethyl-1,5-dichloropentane, etc.

The etherifying conditions for the reaction of a steroid or a zearalin with the dihaloalkane generally include the use of a suitable inert solvent for the reactants. By "inert" is meant a solvent which is substantially nonreactive toward the reactants and the products of the reaction. Advantageous solvents include lower aliphatic alcohols of from 1 to about 4 carbon atoms, such as methanol, ethanol, n-propanol, iso-propanol, n-butanol, and lower aliphatic ketones and amides of from 3 to about 6 carbon atoms, such as acetone, methyl ethyl ketone, dimethylformamide, dimethylacetamide, etc. Methyl ethyl ketone is the preferred solvent for the reaction.

The reaction of a steroid or a zearalin with a dihaloalkane is essentially a nucleophilic substitution of an alkyl halide with a phenoxide ion. To insure a substantial concentration of phenoxide ions, the reaction mixture preferably includes an inorganic salt of a weaker acid than the phenolic steroid or zearalin. Examples of such salts are alkali metal hydroxides and carbonates, e.g. sodium hydroxide, potassium hydroxide, sodium carbonate, potassium carbonate, etc.

The etherifying conditions also advantageously include an elevated temperature sufficiently high to effect the etherification. Generally, a temperature of from about 20° C to about 200° C, preferably from about 40° C to about 100° C insures substantial etherification. A particularly advantageous method for conducting the reaction at an elevated temperature is by refluxing the reaction mixture.

The concentrations of the reactants are not critical to the formation of the steroid ether; however, the starting material, i.e. the steroid or steroid/zearalin mixture, and the dihaloalkane are preferably present in the reaction mixture in a substantially stoichiometric ratio, i.e. from about 1.0 to about 3.0, most preferably about 1.5-2.5 moles of starting material per mole of dihaloalkane.

The reaction is allowed to proceed for a sufficient time to provide substantial production of the steroid ether. Generally, a reaction time of from about 1 hour to about 48 hours, preferably about 8 to 15 hours provides substantial production.

The steroid ether may be recovered from the reaction mixture by any satisfactory means. A convenient method for such recovery is by filtering the mixture while warm to remove the inorganic salts, then cooling the filtrate to effect crystallization of the steroid ether and separating it by filtration or centrifugation. The product may be further purified, e.g. by recrystallization from methyl ethyl ketone, if desired.

The invention is further illustrated by the following examples, which are not intended to be limiting.

EXAMPLE I

Estrone (5.0 g, 1.85 mmole), 1,4-dibromobutane (2.0 g, 0.93 mmole), and anhydrous potassium carbonate (4.0 g) were dispersed in 30 ml of methyl ethyl ketone. The mixture was refluxed for 16 hours. Dimethylformamide (125 ml) was added to the mixture, the methyl ethyl ketone was removed by distillation, and the mixture was refluxed for an additional 9 hours. The dimethylformamide was removed by evaporation under reduced pressure, and the residue was triturated with 150 ml of water. The mixture was filtered and the solid residue was recrystallized from chloroform and cyclohexane. Four grams of light brown crystals were recovered. These crystals were recrystallized once more from the same solvent mixture to give a material having a melting range of 240° C–246° C (decomp) and the following elemental analysis:

| Calc. | ($C_{40}H_{52}O_4$) | Found |
|---|---|---|
| C | 80.49% | 79.32% |
| H | 8.78% | 8.27% |
| O | 10.72% | 11.07% |

NMR and IR spectra were consistent with the following assigned structure:

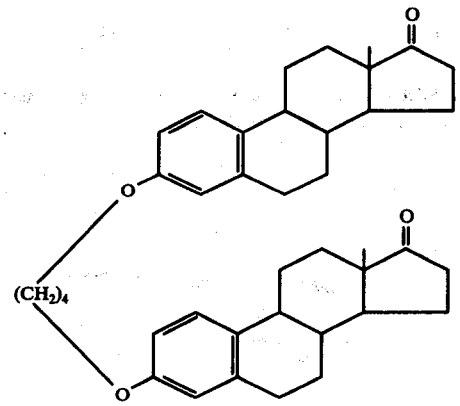

EXAMPLE II

Estrone (4 g, 15 mmole), 1,4-dibromobutane (10 g, 46 mmole), and anhydrous potassium carbonate were dispersed in 100 ml of anhydrous methyl ethyl ketone. The mixture was refluxed for 32 hours, after which unreacted estrone was still found in the reaction mixture. Additional 3 g of potassium carbonate and 10 g of 1,4-dibromobutane were added to the reaction mixture, and refluxing was continued for 40 hours. The mixture was diluted with 100 ml of acetone and filtered while hot. The solids were washed with acetone and combined filtrate and washings were evaporated under reduced pressure and a stream of dry air. The residue was crystallized from cyclohexane to yield 3.3 g of product melting at 97° C–100° C. The NMR spectrum was consistent with the following structure:

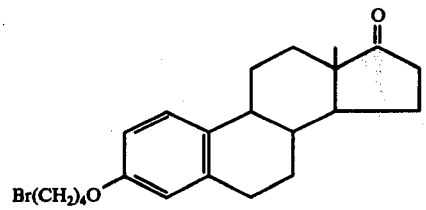

Two grams (5 mmole) of the above product, zearalenone (4.8 g, 15 mmole) and anhydrous potassium carbonate (2.0 g, 14.5 mmole) were dispersed in 100 ml of dry methyl ethyl ketone and refluxed for 27 hours. The mixture was filtered while hot, the solids washed with hot acetone, and the combined filtrate and washings were evaporated under reduced pressure. The residue was dissolved in 100 ml of chloroform. The chloroform was extracted with two 25 ml portions of 20% sodium hydroxide solution to remove unreacted zearalenone. The chloroform was then washed with 25 ml of water and dried over anhydrous sodium sulfate. The chloroform was evaporated under reduced pressure and the residue was recrystallized from hot 2-propanol. The residue was dried at 80° C under vacuum for 15 hours, giving a solid melting at 120° C–128° C. The solid was again recrystallized from cyclohexane containing a small amount of benzene yielding a solid, which, after drying at 80° C for 6 hours under vacuum melted at 107° C–112° C. The elemental analysis of the product was as follows:

| Calc. | ($C_{40}H_{50}O_7$) | Found |
|---|---|---|
| C | 74.73% | 75.17% |
| H | 7.84% | 7.81% |
| O | 17.43% | 17.30% |

The NMR and IR spectra were consistent with the following assigned structure:

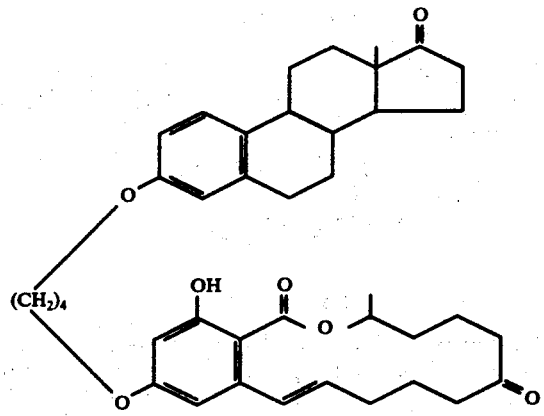

EXAMPLE III

The procedure of Example II is repeated in all essential details except zearalanone is substituted for zearalenone and 2-ethyl-1,4-dibromobutane is substituted for 1,4-dibromobutane. The reaction should yield a product of the formula:

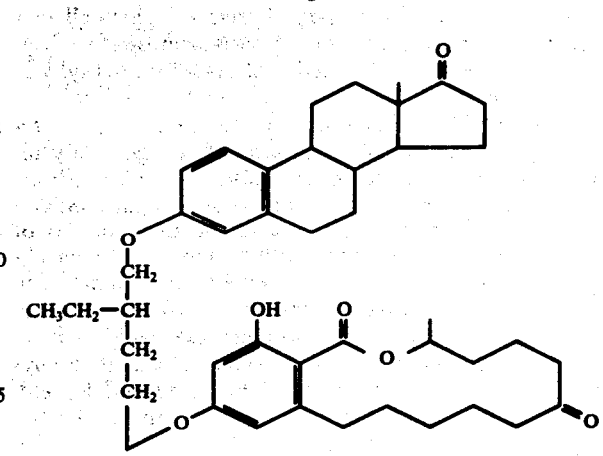

EXAMPLE IV

The procedure of Example II is repeated in all essential details except zearalane is substituted for zearalenone, estradiol is substituted for estrone and 1,5-dichloropentane is substituted for 1,4-dibromobutane. The reaction should yield a product of the formula:

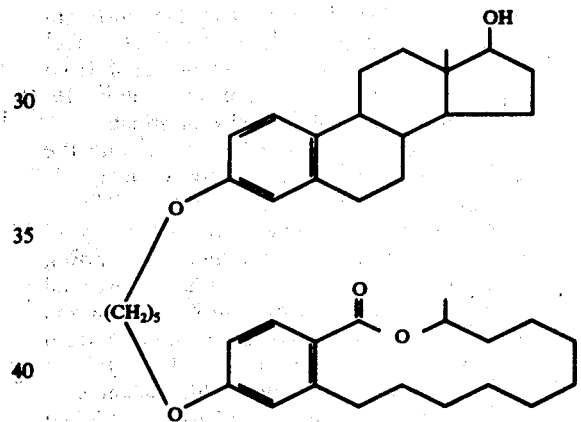

EXAMPLE V

The procedure of Example II is repeated in all essential details except dibenzylzearalanol of the formula:

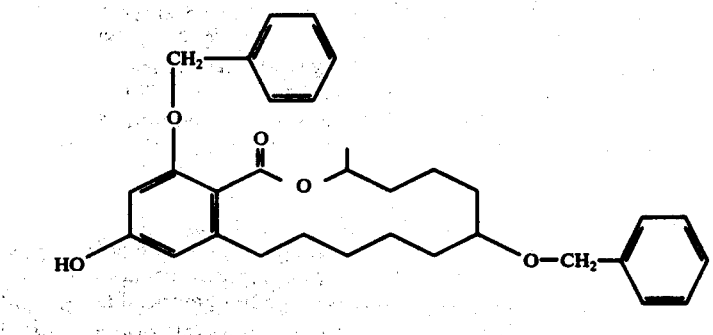

is substituted for zearalenone, estratriol is substituted for estrone, and 2-methyl-1,3-dibromopropane is substituted for 1,4-dibromobutane. The reaction should yield a product of the formula:

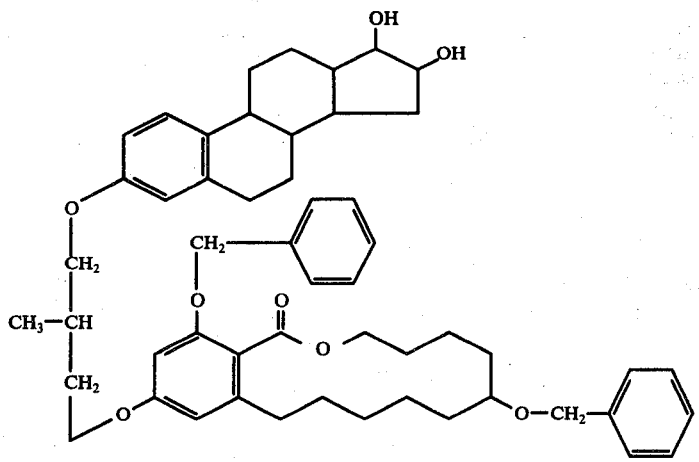

EXAMPLE VI

The following experiment was conducted to determine the estrogenicity of a compound of the formula:

Ovariectomized mice were administered the compound orally in a sesame oil diluent over a three-day period. Control animals were administered sesame oil only, and, for comparison, some animals were administered estrone and some zearalenone in the same manner as the test compounds. The animals were autopsied on the day following the last administration.

Estrogenicity was determined by comparing the uterine weight (as percent of body weight) of the test animals to that of the control animals. The results are summarized in the following table. Each result is an average for ten test animals. The data indicate that the compound possesses estrogenic activity roughly equivalent to that of zearalenone.

|  | Total Dose μg | Final Body Wt (g) | Uterine Weight (% B.W.) |
|---|---|---|---|
| Control (Sesame Oil) | — | 20.13 ±2.03 | 0.047 |
| Test Compound | 150 | 20.63 ±2.56 | 0.095 |
| Test Compound | 300 | 20.25 ±2.43 | 0.0140 |
| Test Compound | 900 | 21.13 ±2.42 | 0.260 |
| Estrone | 18 | 20.75 ±2.77 | 0.174 |
| Zearalenone | 300 | 20.38 | 0.139 |

-continued

|  | Total Dose μg | Final Body Wt (g) | Uterine Weight (% B.W.) |
|---|---|---|---|
|  |  | ±2.67 |  |

EXAMPLE VII

The following experiment was conducted to determine the estrogenicity of a compound of the formula:

Ovariectomized mice were administered the test compound subcutaneously in a sesame oil diluent for four days beginning on the day of ovariectomy. Control animals were administered sesame oil only, and, for comparison, some animals were administered zearalenone in the same manner as the test compound. The animals were autopsied on the day following the last administration. Estrogenicity was determined by comparing the uterine weights (as percent of body weight) of test animals to that of the control animals. The results are summarized in the following table. Each result is an average for eight test animals. The data indicates that the test compound possesses estrogenic activity roughly equivalent to that of zearalenone.

|  | Total Dose (μg) | Final Body Wt (g) | Uterine Weight (% B.W.) |
|---|---|---|---|
| Control (Sesame Oil) | — | 14.9 | 0.120% |
| Test Compound | 160 | 12.9 | 0.196% |
| Test Compound | 320 | 13.0 | 0.320% |

-continued

| | Total Dose (µg) | Final Body Wt (g) | Uterine Weight (% B.W.) |
|---|---|---|---|
| Test Compound | 640 | 12.3 | 0.478% |
| Zearalenone | 160 | 14.4 | 0.243% |
| Zearalenone | 320 | 14.7 | 0.262% |

EXAMPLE VIII

The following experiment was conducted to demonstrate the utility of the following compound as an anti-androgenic agent.

[Chemical structure: two estrone units linked by $(CH_2)_4$ bridge through 3-O positions]

The test compound and testosterone, in carboxymethylcellulose solution diluent, were administered subcutaneously in separate injection sites once daily for seven days to castrate male rats 21 days of age at the start of the test. The animals were autopsied on the day following the last day of treatment.

The androgenic effects of the test compound and the test compound in combination with testosterone were determined by weights of the ventral prostate, the seminal vesicles, and the levator ani. The results, which are summarized in the following table indicate that the test compound has significant anti-androgenic activity. Each test result represents an average for six test animals.

| Treatment Total Dose | Body Weight Initial gm. | Body Weight Final gm. | Ventral Prostate mg | Seminal Vesticles mg | Levator Ani mg |
|---|---|---|---|---|---|
| Controls | 51 | 84 | 13.5 ±0.53 | 10.6 ±0.34 | 20.2 ±1.34 |
| Test Compound 20 µg | 54 | 90 | 15.4 ±0.95 | 11.2 ±0.81 | 23.9 ±0.73 |
| Test Compound 80 µg | 53 | 85 | 14.2 ±0.72 | 11.1 ±0.59 | 24.2 ±1.45 |
| Testosterone 1.0 mg | 53 | 92 | 83.9 ±3.58 | 34.0 ±0.83 | 45.8 ±1.51 |
| Testosterone 1.0 mg + Test Compound 20 µg | 54 | 91 | 68.0 ±3.86 | 38.1 ±1.11 | 44.4 ±2.67 |
| Testosterone 1.0 mg + Test Compound 80 µg | 52 | 91 | 49.5 ±5.29 | 31.9 ±3.37 | 39.8 ±1.50 |

EXAMPLE IX

Six head of cattle are fed a daily ration of alfalfa hay and ground corn cobs containing from 5 to 20 ounces per 100 pounds of feed (3.8 to 15.2 g per kg of feed) of a steroid ether of the following structure:

[Chemical structure: estrone linked via branched alkyl (CH₃CH₂—CH with CH₂—CH₂ chain) to a zearalenone-type macrocyclic resorcylate]

The rates of growth of the cattle should be improved.

EXAMPLE X

The experiment of Example IX is repeated in all essential details except a steroid ether of the following formula is used:

[Chemical structure: estradiol linked through 3-O via $(CH_2)_5$ to a zearalanone-type macrocyclic resorcylate]

The rates of growth of the cattle should be improved.

EXAMPLE XI

The experiment of Example IX is repeated in all essential details except a steroid ether of the following formula is used:

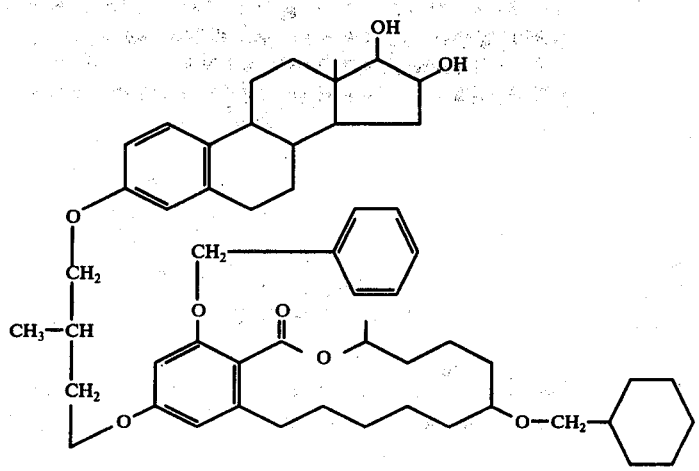

The rates of growth of the cattle should be improved.

I claim:

1. A compound of the formula

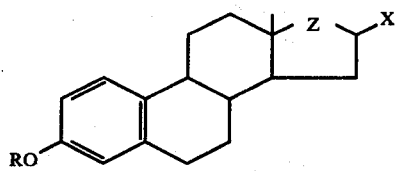

wherein Z is selected from the group consisting of >C=O, >CHOH, and

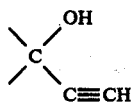

X is selected from the group consisting of —H and —OH, and R is selected from the group consisting of

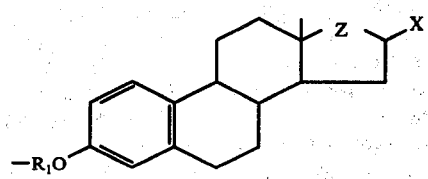

and

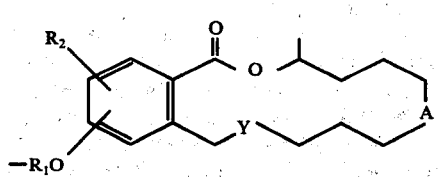

wherein $R_1$ is a straight or branched chain hydrocarbon of from 1 to about 16 carbon atoms; A is selected from the group consisting of —$CH_2$—, >C=O, and >$CHOR_3$; Y may be a single bond or a double bond; $R_2$ and —$R_1O$— represent substituents on the aromatic ring of the group of the second formula, in either the 2 or 4 positions, and $R_2$ is selected from the group consisting of H and $OR_3$; $R_3$ is selected from the group consisting of lower alkyl of from 1 to about 6 carbon atoms; lower acyl of from 1 to about 6 carbon atoms; moncyclic aryl of about 6 to 8 carbon atoms; and monocyclic aralkyl, that is, an alkyl group having an aryl substituent thereon, wherein the alkyl group has 1 to about 5 carbon atoms and the aryl group has about 6 to 8 carbon atoms.

2. A compound of the formula

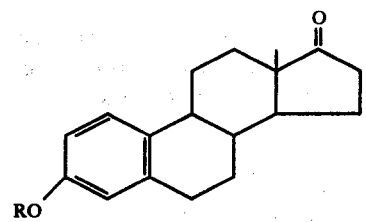

wherein R is selected from the group consisting of

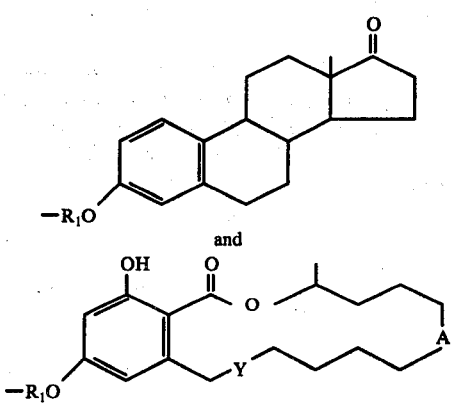

wherein $R_1$ is a straight or branched chain hydrocarbon of from about 2 to about 10 carbon atoms; A is selected from the group consisting of —$CH_2$—, >C=O, and >CHOH; and Y may be a single bond or a double bond.

3. The compound of claim 2 wherein R is a group of the formula

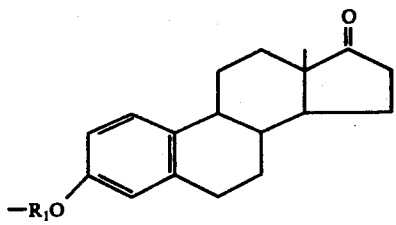

and $R_1$ is a straight or branched chain hydrocarbon of from about 3 to about 6 carbon atoms.

4. The compound of claim 2 wherein R is a group of the formula

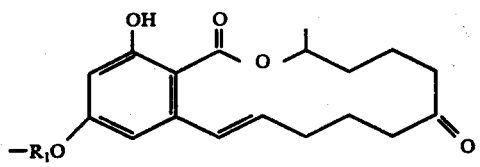

and $R_1$ is a straight or branched chain hydrocarbon of from about 3 to about 6 carbon atoms.

5. The compound of claim 2 wherein R is a group of the formula

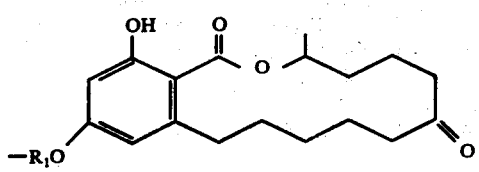

and $R_1$ is a straight or branched chain hydrocarbon of from about 3 to about 6 carbon atoms.

6. The compound of claim 2 wherein R is a group of the formula

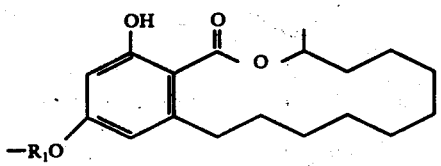

ane $R_1$ is a straight or branched chain hydrocarbon of from about 3 to about 6 carbon atoms.

7. The compound of claim 2 wherein R is a group of the formula

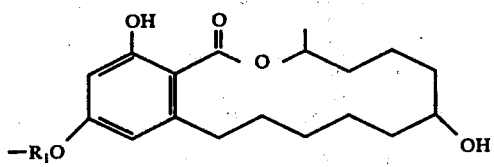

and $R_1$ is a straight or branched chain hydrocarbon of from about 3 to about 6 carbon atoms.

8. A method for making the compound of claim 2 comprising reacting a compound of the formula

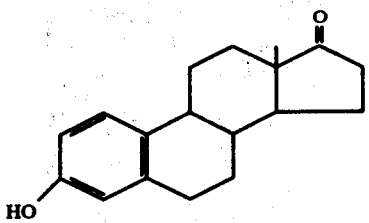

and a compound selected from the group consisting of

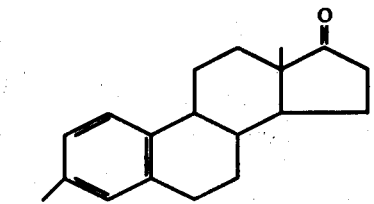

and and

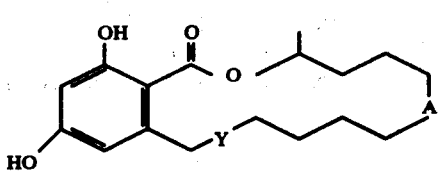

wherein A and Y are defined as in claim 2, with a dihaloalkane having from about 2 to about 10 carbon atoms under etherifying conditions.

9. The method of claim 8 wherein said etherifying conditions include conducting the reaction in an inert solvent, in the presence of an inorganic salt of a weaker acid than the reactants, at an elevated temperature.

10. The method of claim 9 wherein said inert solvent is selected from the group consisting of lower aliphatic alcohols of from 1 to about 4 carbon atoms and lower aliphatic ketones and amides of from about 3 to about 6 carbon atoms; said inorganic salt is selected from the group consisting of alkali metal carbonates and alkali metal hydroxides, and said temperature is from about 20° C to about 200° C.

11. The method of claim 9 wherein said inert solvent is selected from the group consisting of acetone, methyl ethyl ketone, and dimethylformamide, said inorganic salt is selected from the group consisting of sodium carbonate, potassium carbonate, sodium hydroxide, and potassium hydroxide; and said temperature is from about 40° C to about 100° C.

* * * * *

UNITED STATES PATENT AND TRADEMARK OFFICE
CERTIFICATE OF CORRECTION

PATENT NO. : 4,051,128
DATED : September 27, 1977
INVENTOR(S) : Mohammed T. Shipchandler It is certified that error appears in the above-identified patent and that said Letters Patent are hereby corrected as shown below:

Column 2, line 49, "means" should read -- meal --

Column 4, line 26, "6" should read -- 16 --

Column 11, line 52, in the table, fifth column, in the heading "Seminal Vesticles mg" should read -- Seminal Vesicles mg --

Column 12, lines 55-60, that portion of the formula which reads

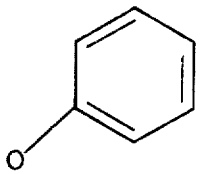     should read     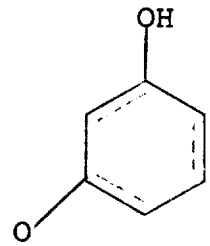

Signed and Sealed this

Thirteenth Day of June 1978

[SEAL]

Attest:

RUTH C. MASON
Attesting Officer

DONALD W. BANNER
Commissioner of Patents and Trademarks